United States Patent [19]
Mavunkel et al.

[11] Patent Number: 6,130,235
[45] Date of Patent: Oct. 10, 2000

[54] COMPOUNDS AND METHODS TO TREAT CARDIAC FAILURE AND OTHER DISORDERS

[75] Inventors: Babu J. Mavunkel, Sunnyvale; John A. Lewicki, Los Gatos; David Y. Liu, Palo Alto; George F. Schreiner, Los Altos Hills, all of Calif.

[73] Assignee: Scios Inc., Mountain View, Calif.

[21] Appl. No.: 09/128,137

[22] Filed: Aug. 3, 1998

Related U.S. Application Data
[60] Provisional application No. 60/086,531, May 22, 1998.

[51] Int. Cl.$^7$ .................. A61K 31/445; C07D 401/06
[52] U.S. Cl. .................. 514/322; 514/321; 514/323; 546/198; 546/199; 546/201
[58] Field of Search .................. 514/321, 322, 514/323; 546/198, 199, 201

[56] References Cited

U.S. PATENT DOCUMENTS

| | | | |
|---|---|---|---|
| 4,088,765 | 5/1978 | Winn et al. | 514/199 |
| 4,243,806 | 1/1981 | Raeymaekers et al. | 544/396 |
| 5,462,934 | 10/1995 | Goto et al. | 514/183 |
| 5,698,553 | 12/1997 | Prucher et al. | 514/222.8 |
| 5,714,498 | 2/1998 | Kulagowski et al. | 514/307 |

FOREIGN PATENT DOCUMENTS

| | | |
|---|---|---|
| 0 318 235 | 5/1989 | European Pat. Off. |
| 0 431 945 | 6/1991 | European Pat. Off. |
| 0 709 384 | 5/1996 | European Pat. Off. |
| 0 831 090 | 3/1998 | European Pat. Off. |
| 2-184673 | 7/1990 | Japan . |
| WO 96/40143 | 12/1996 | WIPO . |
| WO 97/26252 | 7/1997 | WIPO . |
| WO 98/06715 | 2/1998 | WIPO . |
| WO 98/07425 | 2/1998 | WIPO . |
| WO 98/28292 | 7/1998 | WIPO . |

OTHER PUBLICATIONS

Fischer "Physical chemical properties and local anesthetic results of an ether substitute of procaine" CA 67:10051, 1966.

Fischer et al. "Physical –chemical properties and local . . . " CA 67:10051, 1966.

Maguire et al. "The contribution of adenosine to the . . . " CA 92:122605, 1979.

Oelschlaeger et al. "Synthesis of new compounds with . . . " CA 109:73387, 1988.

Harbeson et al. "Inhibition of arginine aminopeptidase . . . " CA 109:162909, 1988.

Eyers, P.A. et al. "Conversion of SB 203580–insensitive MAP kinase family members to drug–sensitive forms by a single amino–acid substitution", *Chem and Biol* (1995) 5:321–328.

Jiang, Y. et al., "Characterization of the structure and function of a new mitogen–activated protein kinase (p38β)" *J Biol Chem* (1996) 271:17920–17926.

Kumar, S. et al. "Novel homologues of CSBP/p38 MAP kinase: activation, substrate specificity and sensitivity to inhibition by pyridinyl imidazoles", *Biochem Biophys Res Comm* (1997) 235:533–538.

Li, Z. et al. "The primary structure of p38γ: a new member of p38 group of MAP kinases", *Biochem Biophys Res Comm* (1996) 228:334–340.

Stein, B. et al. "p38–2, a novel mitogen–activated protein kinase with distinct properties", *J Biol Chem* (1997) 272:19509–19517.

Wang, X.S., et al., "Molecular cloning and characterization of a novel p38 mitogen–activated protein kinase", *J Biol Chem* (1997) 272:23668–23674.

Wang, Y. et al. "Cardiac muscle cell hypertrophy and apoptosis induced by distinct members of the p38 mitogen–activated protein kinase family", *J Biol Chem* (1998) 273:2161–2168.

*Primary Examiner*—Ceila Chang
*Attorney, Agent, or Firm*—Morrison & Foerster LLP

[57] ABSTRACT

The invention is directed to compounds of the formula $$Ar^1-X^1-N\underset{}{\overset{(Y)_n}{\diagup\diagdown}}Z-X^2-Ar^2 \quad (1)$$

and the pharmaceutically acceptable salts thereof
wherein $Ar^1$ is indole, benzimidazole, or benzotriazole, optionally substituted with lower alkyl (1–4C), halo, or lower alkoxy (1–4C);
$X^1$ is CO or an isostere thereof;
Y is optionally substituted alkyl, optionally substituted aryl, or optionally substituted arylalkyl;
n is 0 or 1;
Z is CH or N;
$X^2$ is CH, $CH_2$ or an isostere thereof; and
$Ar^2$ consists of one or two phenyl moieties directly coupled to $X^2$ and optionally substituted by halo, nitro, alkyl (1–6C), CN or $CF_3$, or by RCO, COOR, $CONR_2$, $NR_2$, OR or SR, wherein R is H or alkyl (1–6C) or by phenyl, itself optionally substituted by the foregoing substituents;
with the proviso that if Z is N, $X^1$ is CO, and $Ar^1$ is indole, $Ar^1$ must be coupled to $X^1$ through the 2-, 5-, 6- or 7-position.

These compounds are useful in the treatment of conditions associated with inflammation. In addition, the above compounds and other compounds described herein are useful in treating conditions associated with cardiac failure.

39 Claims, No Drawings

COMPOUNDS AND METHODS TO TREAT CARDIAC FAILURE AND OTHER DISORDERS

This application claimed priority benefit of U.S. Provisional Application Ser. No. 60/086,531 filed May 22, 1998.

TECHNICAL FIELD

The invention is directed to compounds that are useful in treating inflammation and that contain piperazine or piperidine moieties coupled to indole, benzimidazole or benzotriazole. More particularly, the invention concerns novel compounds of this type as well as methods to treat heart and kidney conditions using these and other compounds.

BACKGROUND ART

A large number of chronic and acute conditions have been recognized to be associated with perturbation of the inflammatory response. A large number of cytokines participate in this response, including IL-1, IL-6, IL-8 and TNF. It appears that the activity of these cytokines in the regulation of inflammation rely at least in part on the activation of an enzyme on the cell signaling pathway, a member of the MAP kinase family generally known as p38 and alternatively known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful antiinflammatory agents.

PCT applications WO98/06715, WO98/07425, and WO 96/40143, all of which are incorporated herein by reference, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis, restenosis, cerebral malaria, chronic pulmonary inflammatory disease, silicosis, pulmonary sarcosis, bone resorption diseases such as osteoporosis, graft-versus-host reaction, Crohn's Disease, ulcerative colitis including inflammatory bowel disease (IBD) and pyresis.

The above-referenced PCT applications disclose compounds which are p38 kinase inhibitors said to be useful in treating these disease states. These compounds are either imidazoles or are indoles substituted at the 3- or 4-position with a piperazine ring linked through a carboxamide linkage. Additional compounds which are conjugates of piperazines with indoles are described as insecticides in WO97/26252, also incorporated herein by reference.

DISCLOSURE OF THE INVENTION

The invention is directed to compounds useful in treating inflammation generally, including specific conditions such as those described in the Background section above. Certain novel compounds have been found to inhibit p38 kinase and are thus useful in treating diseases mediated by this enzyme.

The compounds of the invention are of the formula

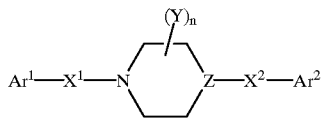

(1)

and the pharmaceutically acceptable salts thereof, wherein $Ar^1$ is indole, benzimidazole, or benzotriazole, optionally substituted with lower alkyl (1–4C), halo, or lower alkoxy (1–4C);

$X^1$ is CO or an isostere thereof,

Y is optionally substituted alkyl, optionally substituted aryl, or optionally substituted arylalkyl;

n is 0 or 1;

Z is CH or N;

$X^2$ is CH, $CH_2$ or an isostere thereof, and $Ar^2$ consists of one or two phenyl moieties directly coupled to $X^2$ and optionally substituted by halo, nitro, alkyl (1–6C), CN or $CF_3$, or by RCO, COOR, $CONR_2$, $NR_2$, OR or SR, wherein R is H or alkyl (1–6C) or by phenyl, itself optionally substituted by the foregoing substituents; with the proviso that if Z is N, $X^1$ is CO, and $Ar^1$ is indole, then $Ar^1$ must be coupled to $X^1$ through the 2-, 5-, 6- or 7-position.

Thus, in one aspect, the invention is directed to compounds of the formula set forth above. In other aspects, the invention is directed to methods to produce these compounds, to pharmaceutical compositions containing them, and to methods of treating inflammation using these compounds. The invention is also directed to treating conditions associated with cardiac failure using the invention compounds and other compounds described herein.

MODES OF CARRYING OUT THE INVENTION

The compounds of formula (1) set forth above are defined by the nature of the substituents on the piperazine or piperidine ring.

$Ar^1$ is an indole, benzimidazole, or benzotriazole nucleus which may be coupled to $X^1$ through any carbon in the ring nucleus. Preferably, however, coupling is through the 5- or 6-position, most preferably through the 5-position. The indole, benzimidazole or benzotriazole nucleus of $Ar^1$ may optionally be substituted with one or two alkyl substituents at any remaining position, preferably at ring nitrogen. Preferred substituents are ethyl, isopropyl, methyl, isobutyl, and t-butyl.

$X^1$ is CO or an isostere thereof. Thus, in addition to CO, $X^1$ may be $CH_2$, SO, $SO_2$, or CHOH. CO is preferred.

Z is CH or N.

$X^2$ is $CH_2$ if $Ar^2$ consists of a single phenyl moiety or CH if $Ar^2$ consists of two phenyl moieties or may be an isostere thereof. Thus, for appropriate embodiments of $Ar^2$, $X^2$ may consist of any of the alternatives set forth above for $X^1$.

The phenyl moieties represented by $Ar^2$ may optionally be substituted by substituents including alkyl (1–6C), halo, RCO, COOR, $CONR_2$, OR, SR, $NR_2$, $NO_2$, CN, or $CF_3$, wherein R is H or alkyl (1–6C). The phenyl moieties may also be substituted with an additional phenyl residue, preferably at the 4-position. The additional phenyl residue may itself be substituted with the substituents set forth above. The additional phenyl may be substituted in all five positions, but preferably less, preferably in 1–2 positions or not at all. Preferred substituents include halo and $OCH_3$. The substituents may occupy all five positions of the phenyl substituent, preferably 1–2 positions or the phenyl may be unsubstituted.

n may be 0 or 1, and is preferably 0. However, when n is 1, Y is present and may be alkyl, arylalkyl or aryl, all of which may optionally be substituted by the substituents set forth above with regard to $Ar^2$. Preferred embodiments of Y include unsubstituted alkyl and unsubstituted arylalkyl.

The compounds of formula (1) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present on the compound of formula (1), the compound may also be supplied as a salt with a pharmaceutically acceptable cation.

Synthesis of the Invention Compounds

The compounds of the invention can be synthesized by first coupling the piperazine or piperidine residue to the indole, benzimidazole or benzotriazole moiety and then coupling with $Ar^2$ or by coupling the already derivatized piperazine or piperidine to the nitrogen-containing bicyclic compound.

Thus, as shown in Reaction Scheme 1, a piperazine protected with tert-butyloxycarbonyl (BOC) is coupled to 5-carboxybenzimidazole in a reaction mixture containing a coupling agent such as EDAC in an inert, aprotic solvent to obtain the coupled carboxamide which is then deprotected and treated with substituted or unsubstituted benzyl halides or benzoyl halides.

Alternatively, as shown in Reaction Scheme 2, carboxylated benzimidazole (or indole or benzotriazole) is reacted with a piperazine or piperidine moiety already substituted by $X^2$-$Ar^2$. In this reaction, the piperazyl or piperadyl derivative is directly reacted with the carboxylated bicycloheteroatom-containing nucleus in the presence of a coupling agent such as EDAC in the presence of an inert solvent as set forth above.

In order to form the substituted piperazine required for Scheme 2, piperazine is first converted to the BOC derivative and then reacted with $Ar^2CHO$ in the presence of a borohydride under acidic conditions to give the substituted piperazine as shown in Reaction Scheme 3.

An alternative for coupling derivatized piperazine or piperidine to indole, benzimidazole or benzotriazole is shown in Reaction Scheme 4. In this reaction, the piperazine or piperidine ring is derivatized to a suitable leaving group as shown and then treated with a reducing agent such as NaH in an inert solvent to obtain the desired conjugate.

Another alternative is shown in Reaction Scheme 5. In this approach, a protected piperidone is reacted under reducing conditions with the appropriate phosphonate ester to obtain a protected benzylene piperidine. The product is then deprotected and reacted with the carboxylate of indole, benzimidazole or benzotriazole using an appropriate dehydrating agent. The product is then reduced to the desired arylalkylated piperidine derivative.

Reaction Scheme 6 illustrates a method for preparing compounds of the invention in which the indole is substituted in the 6-membered ring thereof. In Reaction Scheme 6, the appropriately substituted aniline is reacted with 1-methylmercaptyl-2,2-dialkoxyethane in the presence of tertiary butyryl chloride and base to provide the desired indole. Depending on the nature of the substitution of the aniline starting material, more than one isomer may result as shown. The methylmercaptyl group remaining on the 5-membered ring is reduced with Raney nickel and a mandatory methyl group included on the original aniline moiety is oxidized to the corresponding carboxylic acid. The resulting acid is then reacted with the desired piperidine or piperazine derivative in the presence of a coupling agent such as EDC.

Alkylation of the nitrogens on the indole, benzimidazole or benzotriazole nucleus in the compounds per se is carried out by conventional means using the halide of the substituent to be added in the presence of base and acetone.

Scheme 1

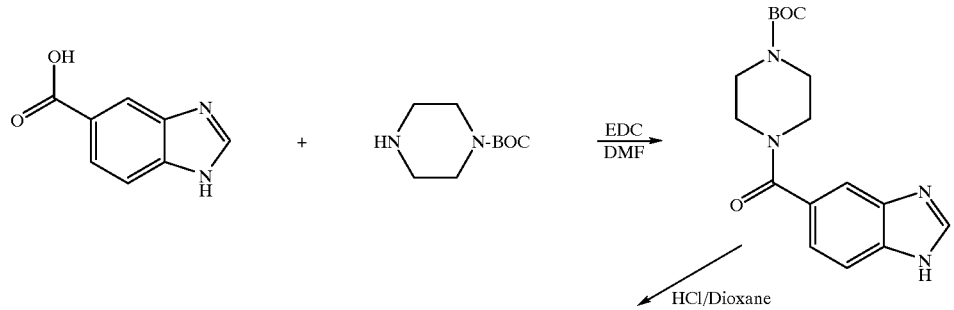

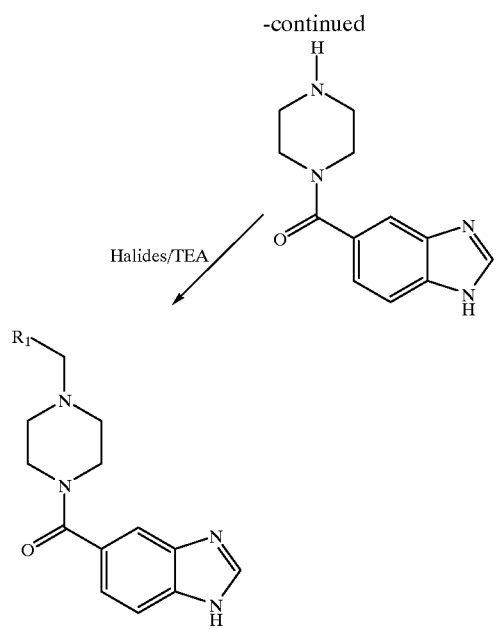

R₁=for example 1,2,6-difluorophenyl; 3,4-difluorophenyl; 2,3-difluorophenyl; 3,5-difluorophenyl, 3-chlorophenyl; 4-carboxymethylphenyl; 4-methoxyphenyl; 4-trifluoromethyloxyphenyl; 4-methylphenyl; 6-chloropiperonyl; t-butylcarboxy; 3-trifluorophenyl.

R₂=for example 1,2,4-dichlorophenyl; 3,4-dichlorophenyl; cyclopentylethyl; trans (3-trifluoromethyl)cinnamoyl; 4-chlorophenyl; phenyl; 2-trifluorophenyl; propyl; methoxyphenyl; p-toluyl.

Scheme 2

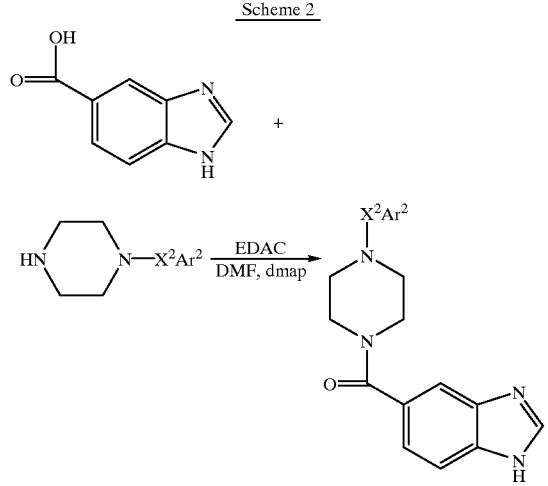

X²Ar² = for example,

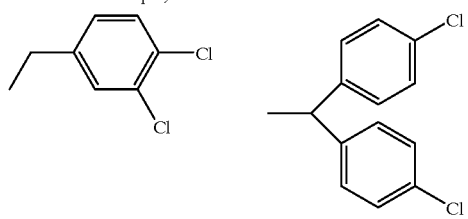

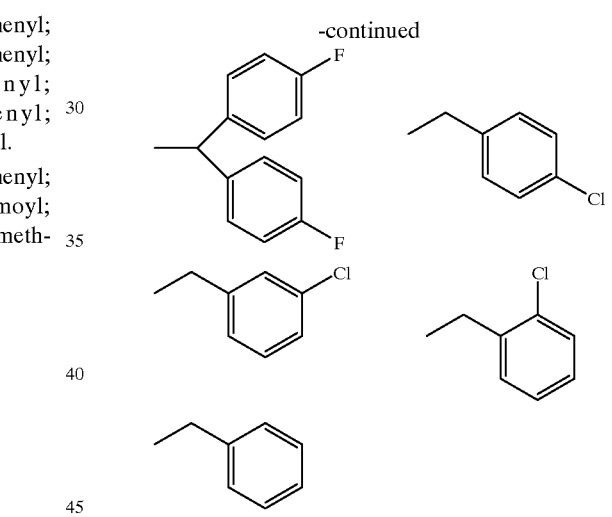

Scheme 3

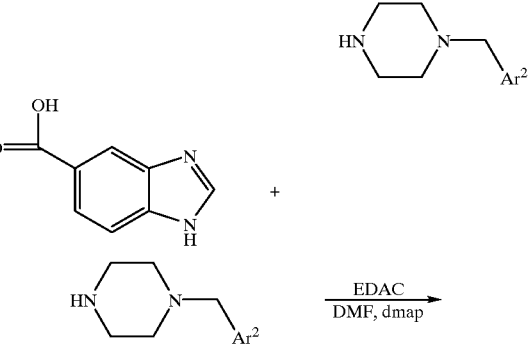

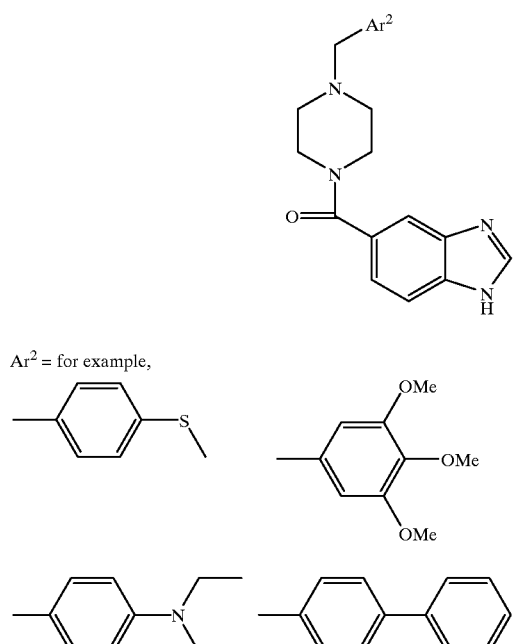
Ar² = for example,
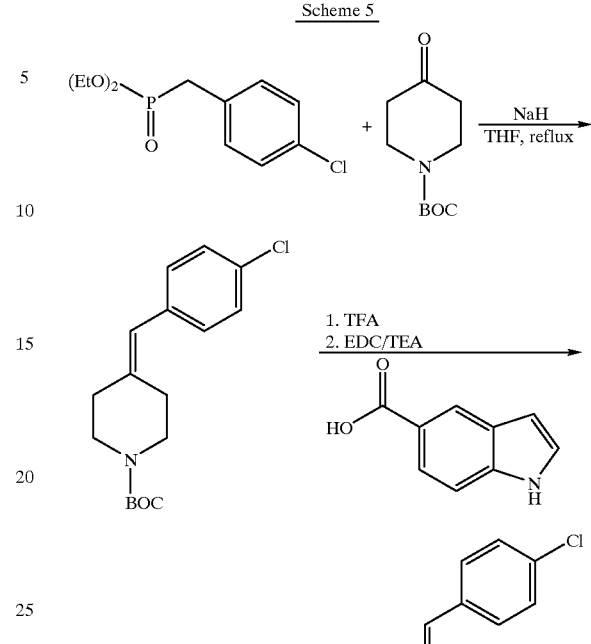
Scheme 5
Scheme 4
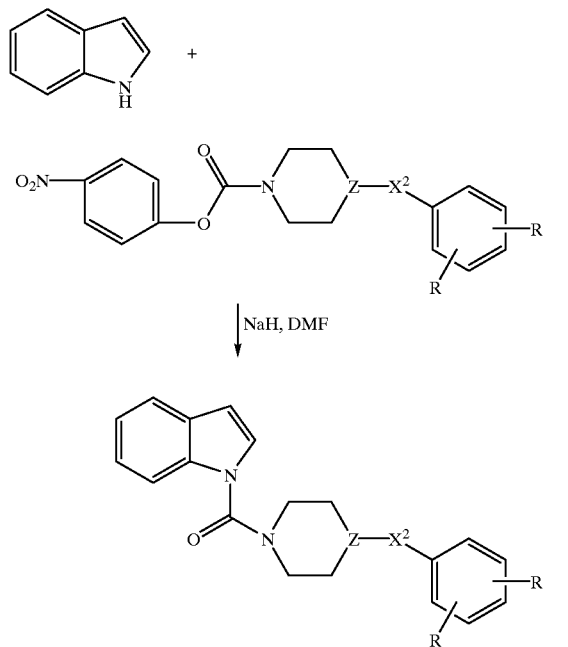
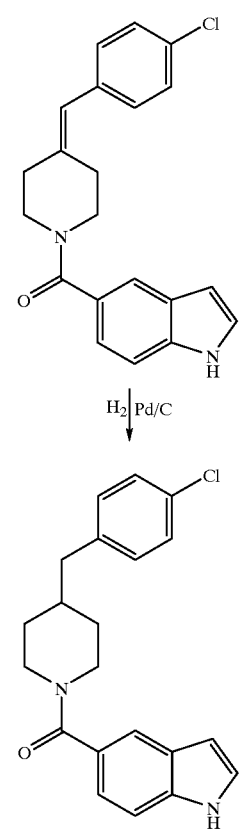

Scheme 6

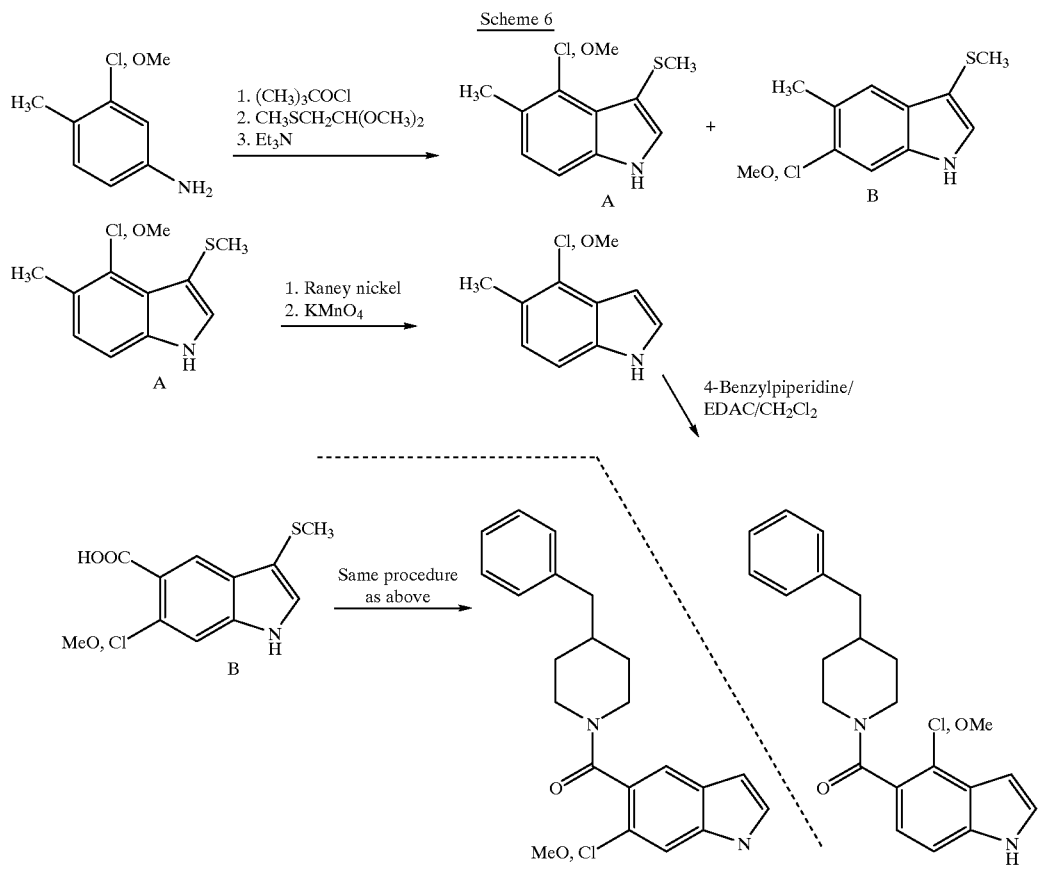

For synthesis of compounds wherein n is 1—i.e., wherein the piperidine ring contains one additional substituent other than those mandated in the compounds of the invention, the 4-substituted piperidine is first protected using BOC$_2$O in THF or other aprotic solvent and then reacted with, for example, an alkyl iodide in the presence of S-butyl lithium/TMEDA using, for example, ether as a solvent to produce the alkylated piperidine. The alkylated piperidine is then converted to the invention compound by deprotection followed by formation of the carboxamido linkage to the indoyl residue. This is exemplified in Example 18 below.

Administration and Use

The compounds of the invention are useful in treating conditions associated with inflammation. Thus, the compounds of formula (1) or their pharmaceutically acceptable salts are used in the manufacture of a medicament for prophylactic or therapeutic treatment of mammals, including humans, in respect of conditions characterized by excessive production of cytokines and/or inappropriate or unregulated cytokine activity on such cells as cardiomyocytes, cardiofibroblasts and macrophages.

The compounds of the invention inhibit the production of cytokines such as TNF, IL-1, IL-6 and IL-8, cytokines that are important proinflammatory constituents in many different disease states and syndromes. Thus, inhibition of these cytokines has benefit in controlling and mitigating many diseases. The compounds of the invention are shown herein to inhibit a member of the MAP kinase family variously called p38 MAPK (or p38), CSBP, or SAPK-2. The activation of this protein has been shown to accompany exacerbation of the diseases in response to stress caused, for example, by treatment with lipopolysaccharides or cytokines such as TNF and IL-1. Inhibition of p38 activity, therefore, is predictive of the ability of a medicament to provide a beneficial effect in treating diseases such as coronary artery disease, congestive heart failure, cardiomyopathy, myocarditis, vasculitis, restenosis, such as occurs following coronary angioplasty, atherosclerosis, rheumatoid arthritis, rheumatoid spondylitis, osteoarthritis, gouty arthritis and other arthritic conditions, multiple sclerosis, acute respiratory distress syndrome (ARDS), asthma, chronic obstructive pulmonary disease (COPD), silicosis, pulmonary sarcosis, sepsis, septic shock, endotoxic shock, toxic shock syndrome, heart and brain failure (stroke) that are characterized by ischemia and reperfusion injury, surgical procedures, such as transplantation procedures and graft rejections, cardiopulmonary bypass, coronary artery bypass graft, CNS injuries, including open and closed head trauma, inflammatory eye conditions such as conjunctivitis and uveitis, acute renal failure, glomerulonephritis, inflammatory bowel diseases, such as Crohn's disease or ulcerative colitis, graft vs host disease, bone resorption diseases like osteoporosis, type II diabetes, pyresis, psoriasis, cachexia, viral diseases such as those caused by HIV, CMV, and Herpes, and cerebral malaria.

Within the last several years, p38 has been shown to comprise a group of MAP kinases designated p38α, p38β, p38γ and p38δ. Jiang, Y. et al. *J Biol Chem* (1996) 271:17920–17926 first reported characterization of p38β as a 372-amino acid protein closely related to p38α. Kumar, S. et al. *Biochem Biophys Res Comm* (1997) 235:533–538 and Stein, B. et al. *J Biol Chem* (1997) 272:19509–19517 reported a second isoform of p38β, p38β2, containing 364 amino acids with 73% identity to p38α. All of these reports show evidence that p38β is activated by proinflammatory cytokines and environmental stress, although the second reported p38β isoform, p38β2, appears to be preferentially expressed in the CNS, heart and skeletal muscle compared to the more ubiquitous tissue expression of p38α. Furthermore, activated transcription factor-2 (ATF-2) was observed to be a better substrate for p38β2 than for p38α, thus suggesting that separate mechanisms of action may be associated with these forms. The physiological role of p38β1 has been called into question by the latter two reports since it cannot be found in human tissue and does not exhibit appreciable kinase activity with the substrates of p38α.

The identification of p38γ was reported by Li, Z. et al. *Biochem Biophys Res Comm* (1996) 228:334–340 and of p38δ by Wang, X., et al., *J Biol Chem* (1997) 272:23668–23674 and by Kumar, S., et al., *Biochem Biophys Res Comm* (1997) 235:533–538. The data suggest that these two p38 isoforms (γ and δ) represent a unique subset of the MAPK family based on their tissue expression patterns, substrate utilization, response to direct and indirect stimuli, and susceptibility to kinase inhibitors.

Various results with regard to response to drugs targeting the p38 family as between p38α and either the putative p38β1 or p38β2 or both were reported by Jiang, Kumar, and Stein cited above as well as by Eyers, P. A. et al. *Chem and Biol* (1995) 5:321–328. An additional paper by Wang, Y. et al. *J Biol Chem* (1998) 273:2161–2168 suggests the significance of such differential effects. As pointed out by Wang, a number of stimuli, such as myocardial infarction, hypertension, valvular diseases, viral myocarditis, and dilated cardiomyopathy lead to an increase in cardiac workload and elevated mechanical stress on cardiomyocytes. These are said to lead to an adaptive hypertrophic response which, if not controlled, has decidedly negative consequences. Wang cites previous studies which have shown that in ischemia reperfusion treated hearts, p38 MAPK activities are elevated in association with hypertrophy and programmed cell death. Wang shows in the cited paper that activation of p38α activity results in hypertrophy, whereas activation of p38α activity leads to myocyte apoptosis. Thus, selective inhibition of p38α activity as compared to p38β activity will be of benefit in treating conditions associated with cardiac failure. These conditions include congestive heart failure, cardiomyopathy, myocarditis, vasculitis, vascular restenosis, valvular disease, conditions associated with cardiopulmonary bypass, coronary artery bypass, grafts and vascular grafts. Further, to the extent that the α-isoform is toxic in other muscle cell types, α-selective inhibitors would be useful for conditions associated with cachexia attributed to TNF or other conditions such as cancer, infection, or autoimmune disease.

Thus, the invention encompasses the use of compounds which selectively inhibit the activity of the p38α isoform for treating conditions associated with activation of p38α, in particular those associated with proinflammation response cardiac hypertrophy, ischemia or other environmental stress such as oxidation injury, hyperosmolarity or other agents or factors that activate p38α kinase, or cardiac failure, for example, congestive heart failure, cardiomyopathy and myocarditis. Compounds useful in these conditions associated with heart failure are of the formula

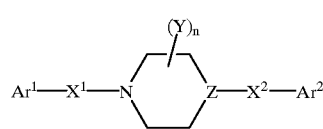

(1)

or a pharmaceutically acceptable salt thereof
wherein $Ar^1$ is indole, benzimidazole, or benzotriazole, optionally substituted with lower alkyl (1–4C), halo, or alkoxy (1–4C);
$X^1$ is CO or an isostere thereof;
Y is optionally substituted alkyl, optionally substituted aryl, or optionally substituted arylalkyl;
n is 0 or 1;
Z is CH or N;
$X^2$ is CH, $CH_2$ or an isostere thereof; and
$Ar^1$ consists of one or two phenyl moieties directly coupled to $X^2$ and optionally substituted by halo, nitro, alkyl (1–6C), CN or $CF_3$, or by RCO, COOR, $CONR_2$, $NR_2$, OR or SR, wherein R is H or alkyl (1–6C) or by phenyl, itself optionally substituted by the foregoing substituents.

The manner of administration and formulation of the compounds useful in the invention and their related compounds will depend on the nature of the condition, the severity of the condition, the particular subject to be treated, and the judgement of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%–95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences*, latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001–100 mg/kg total body weight, preferably from 0.01–50 mg/kg and more preferably about 0.01 mg/kg–10 mg/kg. The dose regimen will vary, however, depending on the conditions being treated and the judgment of the practitioner.

As implicated above, although the compounds of the invention may be used in humans, they are also available for veterinary use in treating animal subjects.

The following examples are intended to illustrate but not to limit the invention.

Examples 1–3 illustrate Reaction Scheme 1:

EXAMPLE 1

Preparation of 4-BOC piperazinyl-benzimidazole-5-carboxamide

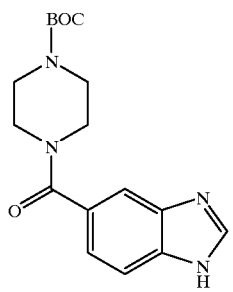

Benzimidazole-5-carboxylic acid (3.25 g, 20 mMol) was reacted with 2.52 g (20 mMol) diisopropylcarbodiimide in dry DMF at room temperature for 15 minutes. To this reaction mixture was added 3.75 g (20 mMol) t-butyl-1-piperazine carboxylate, and the mixture was stirred for 18 h. The mixture was poured into water and extracted with methylene chloride (3×100 mL). The combined extracts were washed again with water, brine and dried over MgSO$_4$. After removal of the solvent in vacuo, the residue was chromatographed on a column of silica gel eluting with CHCl$_3$-Methanol (gradient, methanol 0 to 5%) to yield 5.69 g (86%) of the product. $^1$H-NMR (DMSO d$_6$): s 8.3 (1H); m 7.7–7.6 (2H), m 7.2–7.3 (1H), m 3.6–3.3 (8H) s 1.4 (9H); MS (ESI) m/e 330 (m$^+$).

EXAMPLE 2

Preparation of piperazinyl-benzimidazole-5-carboxamide

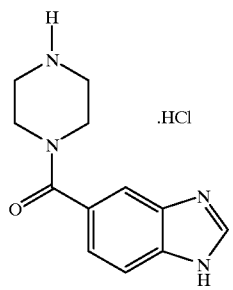

The N-BOC piperazinyl-benzimidazole-5-carboxamide (5.6 g) was stirred in 20 mL 4 Molar HCl-dioxane for 1 h. The dioxane was removed under reduced pressure to yield the hydrochloride salt in quantitative yield. This was used for alkylations without any further purifications.

EXAMPLE 3

Preparation of 4-(2,6-difluorobenzyl)-piperazinyl-benzymidazole-5-carboxamide

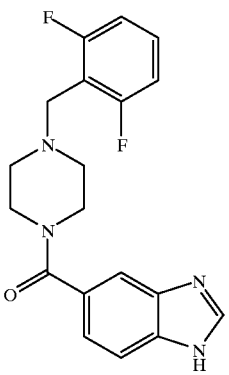

A. Piperazinyl-benzimidazole-5-carboxamide (0.186 g, 0.5 mMol) was taken in 5 mL DMF and 0.101 g (1 mMol) triethylamine was added and stirred for 15 minutes at room temperature. To this reaction mixture was added 0.104 g 2,6-difluorobenzyl bromide and the mixture was stirred for 20 h. This was poured into water and extracted with methylene chloride (3×50 mL). The combined extract was further washed with brine, water and dried over MgSO$_4$. The solvent was removed in vacuo and the residue chromatographed on silica gel eluting with chloroform-methanol (0 to 5% methanol, gradient). Evaporation of the desired fraction gave 48.9 mg of the desired product; MS(ESI) m/e 356 (M$^+$).

B. Using the procedure set forth in paragraph A, the following compounds were prepared:

| Preparation of | By substituting for 2,6-difluorobenzyl bromide: |
|---|---|
| 4-(2,3-difluorobenzyl)-piperazinyl-benzimidazole-5-carboxamide MS (ESI) m/e 356 (M$^+$) | 2,3-difluorobenzyl bromide |
| 4-(3,5-difluorobenzyl)-piperazinyl-benzimidazole-5-carboxamide MS (ESI) m/e 356 (M$^+$) | 3,5-difluorobenzyl-bromide |
| 4-(3-chlorobenzyl)-piperazinyl-benzimidazole-5-carboxamide MS (ESI) m/e 354 (M$^+$) | 3-chlorobenzyl bromide |
| 4-(4-carboxymethyl benzyl)-piperazinyl-benzimidazole-5-carboxamide MS (ESI) m/e 378 (M$^+$) | methyl-4-(bromomethyl)-benzoate |
| 4-(4-methoxybenzyl)-piperazinyl-benzimidazole-5-carboxamide MS (ESI) m/e 350 (M$^+$) | 4-methoxybenzyl chloride |
| 4-(4-trifluoromethoxybenzyl)-piperazinyl-benzimidazole-5-carboxamide MS (ESI) m/e 404 (M$^+$) | 4-(4-trifluoromethoxy)-benzyl bromide |
| 4-(4-methylbenzyl)-piperazinyl-benzimidazole-5-carboxamide MS (ESI) m/e 334 (M$^+$) | 4-methylbenzyl bromide |
| 4-(6-chloropiperonyl)-piperazinyl-benzimidazole-5-carboxamide MS (ESI) m/e 399 (M$^+$) | 6-chloropiperonyl chloride |
| 4-(4-t-butylcarboxymethyl)- | t-butyl |

| Preparation of | By substituting for 2,6-difluorobenzyl bromide: |
|---|---|
| piperazinyl-benzimidazole-5-carboxamide MS (ESI) m/e 344 (M+) | bromoacetate |
| 4-(2,4-dichlorobenzoyl)-piperazinyl-benzimidazole-5-carboxamide MS (ESI) m/e 403 (M+) | 2,4-dichlorobenzoyl chloride |
| 4-(3,4-dichlorobenzoyl)-piperazinyl-benzimidazole-5-carboxamide MS (ESI) m/e 403 (M+) | 3,4-dichlorobenzoyl chloride |
| 4-(3-cyclopentylpropionyl)-piperazinyl-benzimidazole-5-carboxamide MS (ESI) m/e 354 (M+) | 3-cyclopentylpropionyl chloride |
| 4-(cyclohexycarbonyl)-piperazinyl-benzimidazole-5-carboxamide MS (ESI) m/e 340 (M+) | 3-cyclohexanecarbonyl chloride |
| 4-[trans-3-(trifluoromethyl)-cinnamoyl]-piperazinyl-benzimidazole-5-carboxamide MS (ESI) m/e 428 (M+) | trans-3-(trifluoromethyl)-cinnamoyl chloride |
| 4-(4-chlorobenzoyl)-piperazinyl-benzimidazole-5-carboxamide MS (ESI) m/e 369 (M+) | 4-chlorobenzoyl chloride |
| 4-benzoylpiperazine-benzimidazole-5-carboxamide MS (ESI) m/e 334 (M+) | benzoyl chloride |
| 4-(2-trifluoromethylbenzoyl)-piperazinyl-benzimidazole-5-carboxamide MS (ESI) m/e 402 (M+) | 2-(trifluoromethyl)-benzoyl chloride |
| 4-(4-methxybenzoyl)-piperazinyl-benzimidazole-5-carboxamide MS (ESI) m/e 364 (M+) | 4-methoxybenzoyl chloride |

Example 4 illustrates Reaction Scheme 2:

EXAMPLE 4

Preparation of 4-(3,4-dichlorophenyl)-piperazinyl-benzimidazole-5-carboxamide A. Benzimidazole-5-carboxylic acid (1 mMol, 162 mg) was dissolved in 5 mL dry DMF and reacted with 1-ethyl-3-(3-dimethylaminopropyl)-carbodiimide hydrochloride for 15 minutes. 1-(3,4-dichlorophenyl )-piperazine, 1 mMol (231 mg) was added followed by 10 mg DMAP. The mixture was stirred for 20 h at room temperature. The reaction mixture was poured into water and extracted with methylene chloride (3×50 mL). The extracts were combined, washed with brine, water and dried over MgSO$_4$. After evaporation of the solvent, the residue was chromatographed on silica gel with chloroform-methanol (0–5% methanol, gradient). Evaporation of the desired fractions gave 150 mg (40%) of the title compound; MS (ESI) m/e 375 (M+).

B. Using the procedure of paragraph A, the following were prepared:

| Preparation of | Substituting for 1-(3,4-dichlorophenyl) piperazine, |
|---|---|
| 4-(4-chlorobenzhydryl)-piperazinyl-benzimidazole-5-carboxamide MS (ESI) m/e 431 (M+) | 1-(4-chlorobenzhydryl)-piperazine |
| 4-trans-1-cinnamyl piperazinyl-benzimidazole-5-carboxamide MS (ESI) m/e 346 (M+) | trans-1-cinnamyl piperazine |
| 4-(4-chlorophenyl)-piperazinyl-benzimidazole-5-carboxamide MS (ESI) m/e 341 (M+) | 1-(4-chlorophenyl)-piperazine |
| 4-[bis(4-fluorophenyl)-methyl]-piperazinyl-benzimidazole-5-carboxamide MS (ESI) m/e 432 (M+) | 1-Bis (4-fluorophenyl)-methyl piperazine |
| 4-(4-chlorobenzyl)-piperazinyl-benzimidazole-5-carboxamide MS (ESI) m/e 354 (M+) | 1-(4-chlorobenzyl)-piperazine |
| 4-(2-chlorobenzyl)-piperazinyl-benzimidazole-5-carboxamide MS (ESI) m/e 354 (M+) | 1-(2-chlorobenzyl)-piperazine |
| 4-benzylpiperazinyl-benzimidazole-5-carboxamide MS (ESI) m/e 320 (M+) | 1-benzyl piperazine |

Example 5 illustrates Reaction Scheme 3:

EXAMPLE 5

Preparation of 4-(4-methylthiobenzyl)-piperazinyl-benzimidazole-5-carboxamide

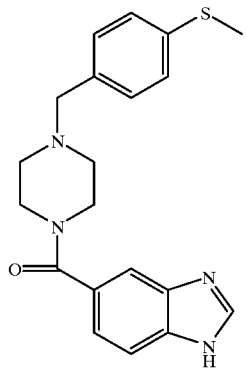

A. A mixture of 4-(methylthio)-benzaldehyde, 305 mg (2 mMol) and N-BOC piperazine, 372 mg (2 mMol) was stirred in dry methanol for 30 minutes. To this mixture was added 1.6 g of polymer-supported borohydride (2.5 mMol/g, on Amberlite, IRA-400, Aldrich) and the mixture was stirred for 24 h. The polymer was removed by filtration and evaporation of the solvent yielded the 4-BOC-1-(4-methylthio)-benzylpiperazine in quantitative yield. MS (ESI) m/e 322, (M+).

The 4-BOC-1-(4-methylthio)-benzylpiperazine was taken in 10 mL 1:1 TFA/methylene chloride and stirred for 1 h at room temperature. The solvents were removed in vacuo and the residue was used without purification for coupling with benzimidazole-5-carboxylic acid.

Benzimidazole-5-carboxylic acid (2 mMol, 324 mg) was taken in 15 mL dry DMF and reacted with 2 mMol (382 mg) EDAC at room temperature for 15 minutes. The above described 1-(4-methylthio)-benzylpiperazine was added as a DMF solution followed by 505 mg (5 mMol) TEA. The mixture was stirred for 20 h. The mixture was poured into water and extracted with methylene chloride (3×50 mL). The combined extracts were washed with brine, water and dried over MgSO$_4$. The solvent was removed in vacuo and the residue was chromatographed. Evaporation of the desired fractions gave the title compound; MS (ESI) m/e 366 (M$^+$).

B. Using the procedure of paragraph A, the following were prepared:

| Preparation of | Substituting for 4-(methylthio)-benzaldehyde |
| --- | --- |
| 4-(3,4,5-trimethoxybenzyl)-piperazynyl-benzimidazole-5-carboxamide MS (ESI) m/e 410 (M$^+$) | 3,4,5-methoxybenzaldehyde |
| 4-(2-naphthylmethyl)-piperazynyl-benzimidazole-5-carboxamide MS (ESI) m/e 370 (M$^+$) | 2-naphthaldehyde |
| 4-(4-diethylaminobenzyl)-piperazinyl-benzimidazole-5-carboxamide MS (ESI) m/e 391 (M$^+$) | 4-diethylamino-benzaldehyde |
| 4-(biphenylmethyl)-piperazinyl-benzimidazole-5-carboxamide MS (ESI) m/e 396 (M$^+$) | 4-biphenylcar-boxaldehyde |
| 4-(4-Phenoxybenzyl)-piperazinyl-benzimidazole-5-carboxamide MS (ESI) m/e 412 (M$^+$) | 4-phenoxy-benzaldehyde |
| 4-(4-quinolinylmethyl)-piperazinyl-benzimidazole-5-carboxamide MS (ESI) m/e 371 (M$^+$) | 4-quinoline-carboxaldehyde |

EXAMPLE 6

Preparation of 4-(4-benzyl)-piperidinyl-benzimidazole-5-carboxamide

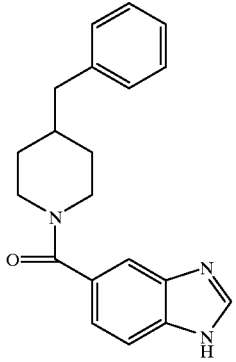

Benzimidazole-5-carboxylic acid (1.62 g, 10 mMol) was reacted with EDAC (1.92 g, 10 mMol) in 40 mL dry DMF at room temperature for 15 minutes. To the reaction mixture was added 4-benzylpiperidine (1.75 g, 10 mMol) and DMAP (~20 mg, catalyst) and the mixture was stirred at room temperature for 20 h. It was poured into water and extracted with methylene chloride (3×100 mL). The combined extract was washed with water, brine and again with water. The extract was dried over MgSO$_4$ and evaporated. The residue was chromatographed on a column of silica gel with chloroform-methanol (0 to 5% methanol). Evaporation of the desired fractions gave 1.5 g (47%) of the product after recrystallization from ethyl acetate-hexane. $^1$HNMR (CDCl$_3$): δ=7.8 (s, 1H); 7.1–7.3 (m, 8H); 4.8–4.7 (broad m, 1H), 3.7–3.9 (broad m, 1H); 3.1–2.7 (broad m, 2H); 2.55 (d, 2H); 2.0–1.1 (m, 5H). MS (ESI) m/e 319 (M$^+$), 318 (M$^+$—H).

EXAMPLE 7

N-propylation of 4-(4-benzyl)-piperidinyl-benzimidazole-5-carboxamide

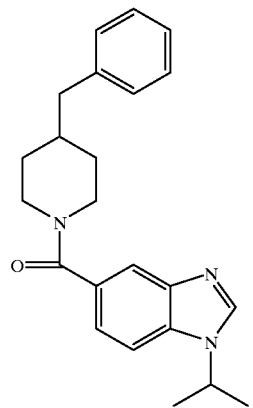

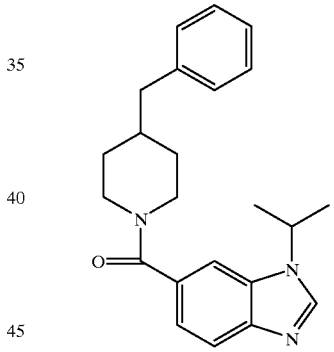

4-(4-Benzyl)-piperidinyl-benzimidazole-5-carboxamide (318 mg, 1 mMol) was taken in 20 mL acetone. KOH (solid, 280 mg, 5 mMol) was added followed by 2-iodopropane (1 g~6 mMol) and the mixture was refluxed for 20 h. The acetone was removed in vacuo and the residue extracted from water with methylene chloride (3×50 mL). The extract was dried, evaporated and the residue chromatographed on silica gel with CHCL$_3$-Methanol (0 to 3% methanol). MS (ESI) m/e 360 (M$^+$). HPLC: (Vydac C18 column, 5 to 40% acetonitrile/water containing 0.1% TFA) two peaks showing both isomers.

EXAMPLE 8

Preparation of 4-benzylpiperidinyl-indole-5-carboxamide

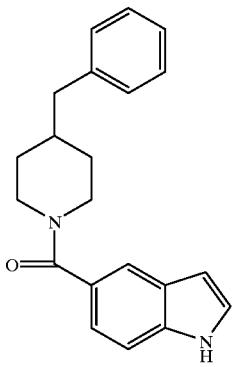

Indole-5-carboxylic acid (1.61 g, 10 mMol) was reacted with EDAC (1.92 g, 10 mMol) in 40 mL dry DMF for 15 minutes. 4-Benzylpiperidine (1.75 g, 10 mMol) was added followed by DMAP (20 mg, catalyst) and the reaction mixture was stirred for 20 h. The mixture was poured into water and extracted with methylene chloride (3×100 mL). The combined extract was washed with dilute hydrochloric acid, saturated sodium bicarbonate and water and dried over MgSO$_4$. After evaporation of the solvent, the residue was chromatographed with methylene chloride-methanol (0 to 2% methanol, gradient) to yield 1.60 g (50%) of the product after recrystallization from ether-Hexane. MS (ESI) m/e 318 (M$^+$), (317$^+$—H). $^1$HNMR (CDCl$_3$)δ=8.5 (s, 1H); 7.7 (s, 1H), 7.4–7.15 (m, 8H); 6.8 (s, 1H); 4.8–4.6 (br, m, 1H); 4.1–3.9 9br, m, 1H); 3.1–2.7 (br, m, 2H); 2.6 (d, 2H); 1.9–1.7 (br, m, 3H); 1.4–1,2 (br, m, 2H).

EXAMPLE 9

Preparation of 4-benzylpiperidinyl-1-(2-propyl)-indole-5-carboxamide

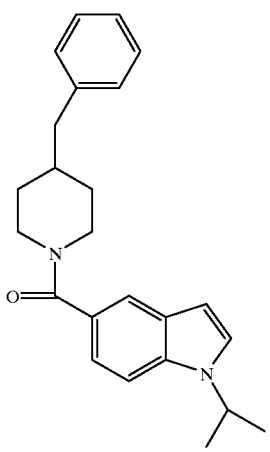

A mixture of 4-benzylpiperidinyl-benzimidazole-5-carboxamide (318 mg, 1 mMol), solid KOH (280 mg, 5 mMol) and 2-iodopropane (1 g, 6 mMol) was refluxed in 20 mL acetone for 20 h. After the removal of acetone in vacuo, the residue was extracted from water with methylene chloride (3×50 mL). The combined extract was dried, evaporated and chromatographed to yield 180 mg (50%) of the desired product. $^1$HNMR (CDCl$_3$): δ=7.7 (s, 1H); 7.4–7.1 (m, 7H); 4.8–4.6 (m, 1H); 3.0–2.7 (br, m, 4H); 2.6 (d, 2H); 1.8–1.45 (m, 3H); 1.5 (d, 6H); 1.3–1.1 (m, 2H). MS (ESI) m/e 360 (M).

EXAMPLE 10

Preparation of 4-(4-chlorobenzyl)-piperazinyl-1-(2-propyl)-indole-5-carboxamide

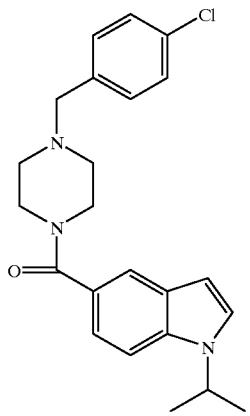

4-(4-Chlorobenzyl)piperazinyl-indole-5-carboxamide (420 mg, 1.32 mMol) was taken in acetone. Solid KOH (280 mg, 5 mMol) was added followed by the addition of 2-iodopropane (1 g, 6 mMol) and the mixture was refluxed with stirring for 20 h. Acetone was removed in vacuo and the residue was extracted from water using methylene chloride. The extract was dried and evaporated and the residue was chromatographed on a column of silica gel using ethylacetate-hexane (ethylacetate 0 to 25%, gradient) and recrystallized from ether-hexane to yield 300 mg of the product. $^1$HNMR (CDCl$_3$): δ=7.6 (s, 1H); 7.3–7.1 (m, 6H); 6.5 (s, 1H); 4.65–4.55 (m, 1H); 3.8–3.5 (m, 4H); 3.4 (s, 2H); 2.4–2.5 (s, 4H); 1.5 (d, 6H). MS (ESI) m/e 395 (M$^+$).

EXAMPLE 11

Preparation of Additional Analogs

Additional analogs wherein the piperidinyl moiety is conjugated to other positions of the indole nucleus were also prepared, as well as their N-alkylated forms. In general, the procedures set forth in Example 8 (for the conjugation) and Example 10 (for the alkylation) were employed. The compounds prepared are summarized below:

Using the procedure of Example 8, the positional analogs are prepared; as well as benzotriazole derivatives.

| Preparation of | Using the procedure set forth in Example 8, but substituting for indole-5-carboxylic acid |
|---|---|
| 4-benzylpiperidinyl-indole-6-carboxamide MS (ESI) m/e 318 (M$^+$), (317$^+$-H) | Indole-6-carboxylic acid |
| 4-benzylpiperidinyl-indole-3-carboxamide MS (ESI) m/e 318 (M$^+$), (317$^+$-H) | Indole-3-carboxylic acid |
| 4-benzylpiperidinyl-indole-4-carboxamide MS (ESI) m/e 318 (M$^+$), (317$^+$-H) | Indole-4-carboxylic acid |

-continued

| Preparation of | Using the procedure set forth in Example 8, but substituting for indole-5-carboxylic acid |
|---|---|
| 4-benzylpiperidinyl-indole-7-carboxamide MS (ESI) m/e 318 (M+), (317+-H) | Indole-7-carboxylic acid |
| 4-benzylpiperidinyl-benzotriazole-5-carboxamide MS (ESI) m/e 320 (M+), (319+-H) | Benzotriazole-5-carboxylic acid |

Using the procedure of Example 10, these compounds were alkylated, e.g.,

| Preparation of | Using the procedure set forth in Example 11, but substituting for 4-chlorobenzyl piperidinyl indole-5-carboxamide |
|---|---|
| 4-benzylpiperidinyl-1-(2-propyl)-indole-6-carboxamide MS (ESI) m/e 360 (M+) | 4-benzyl piperidinyl-indole-6-carboxamide |
| 4-benzylpiperidinyl-1-(2-propyl)-indole-3-carboxamide MS (ESI) m/e 360 (M+) | 4-benzyl piperidinyl-indole-3-carboxamide |

EXAMPLE 12

Preparation of 4-benzylpiperidinyl-indole-1-carboxamide

A. Preparation of 4-benzylpiperidinyl-p-nitrophenyl carbamate

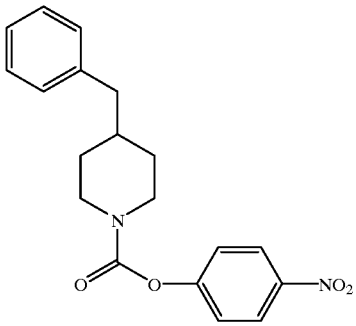

To a mixture of 4-benzylpiperidine (1.76 mL, 10 mMol) and triethylamine (2.78 mL, 20 mMol) in 20 mL of dichloromethane cooled to 0° C. was added a solution of 4-nitrophenyl chloroformate (2.22 g, 11 mMol) in 10 mL dichloromethane. The mixture was stirred for 3 h at room temperature, poured into water and extracted with ethylacetate (3×50 mL). The combined extracts were washed with 1M HCl, 1M aqueous NaOH, water and brine. After drying over $Na_2SO_4$, evaporation of the solvent gave the desired product as a tan solid. Yield: 3.29 g, 96.7%. $^1$HNMR ($CDCl_3$) δ=8.27–8.2 (m, 2H); 7.35–7.13 (m, 7H); 4.25 (br, s, 2H); 3.1–2.75 (m, 2H); 2.65–2.55 (m, 2H); 1.85–1.70 (m, 3H); 1.35–1.20 (m, 2H). MS (ESI) m/e 340 (M+).

B. Reaction of Indole with 4-Benzylpiperidinyl-p-nitrophenyl carbamate

To a suspension of 60% NaH (0.08 g, 2 mMol) in 5 mL THF at RT was added a solution of indole (0.205 g, 1.75 mMol) in THF (5 mL). After stirring at RT for 30 minutes, a solution of the nitrophenyl carbamate (0.51 g, 1.5 mMol) in 5 mL THF was added. The mixture was stirred at RT for 1 h, poured into water and extracted with ethyl acetate (3×50 mL). The combined extracts were washed with 1 M aq. NaOH, 1 M aq. HCl, water and brine. After drying over $Na_2SO_4$, the solvent was evaporated and the residue was purified by chromatography on silica gel using acetone-hexane (5:95). Evaporation of the desired fractions gave 0.4 g (84%) of the desired product as a viscous oil. MS (ESI) m/e 318 (M+).

EXAMPLE 13

Preparation of 4-Benzylpiperidinyl-indole-2-carboxamide and its 1-isopropyl derivative

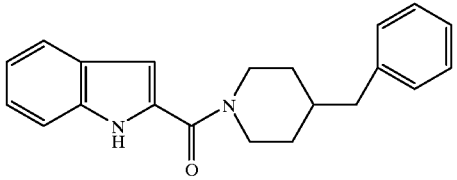

To a solution containing 1.0 g (6.2 mMol) of indole-2-carboxylic acid and 1.1 g (6.2 mMol) of 4-benzylpiperidine in 20 mL of DCM was added 1.3 g (6.5 mMol) of EDC. The mixture was stirred at RT overnight. The solvent was evaporated and the residue was taken up in EtOAc and washed with dil. HCl, 10% $NaHCO_3$ and brine. The organic layer was dried with $NaSO_4$ and concentrated. On crystallization from 10% MeOH in EtOAc provided 1.8 g (91%) of product as white solids, NMR (DMSO-$d_6$) δ=1.21 (m, 4H), 1.63 (d, 2H), 1.85 (m, 1H), 2.58 (d, 2H), 2.82–3.12 (br, 2H), 4.43 (d, 2H), 6.71(s, 1H), 7.05 (t, 1H), 7.21(m, 4H), 7.32 (m, 2H), 7.22 (d, 1H), 7.64 (d, 1H), 11.55 (s, 1H). MS (ESI) m/e 318 (M+).

To a solution of 200 mg (0.63 mMol) of 4-benzylpiperidinyl-indole-2-carboxamide in 10 ml of acetone was added 321 mg (1.9 mMol) of 2-iodopropane and 106 mg (1.9 mMol) of powdered KOH. The mixture was refluxed for 3 h, then cooled, evaporated and the crude product was purified by silica gel column chromatography using EtOAc:hexane (1:4) to provide the 4-Benzylpiperidinyl-1-(2-propyl)-indole-2-carboxamide as white solids, NMR (DMSO-$d_6$) δ=1.15 (m, 2H), 1.60 (d, 6H), 1.82 (m, 4H), 2.56 (d, 2H), 2.72 (m, 1H), 3.02 (m, 1H), 4.15 (m, 1H), 4.80 (m, 1H), 6.45 (s, 1H), 7.05–7.32 (m, 7H), 7.52 (d, 1H), 7.61 (d, 1H). MS (ESI) m/e 360 (M+).

EXAMPLE 14

Preparation of 4-Chlorobenzylpiperazinyl)-indole-2-carboxamide

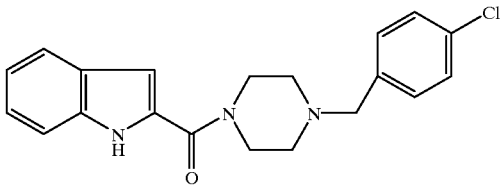

A. A solution containing 1.0 g (6.2 mMol) of indole-2-carboxylic acid, 1.2 g (6.2 mMol) of BOC-piperazine, 1.2 g (6.2 mMol) EDC in 20 mL DCM was stirred overnight. The solvent was evaporated and the residue was taken up in EtOAc and washed with dil. HCl, 10% NaHCO₃, and brine. The organics are dried with Na₂SO₄ and evaporated to get 1.92 g (94%) of amide as white solids. The BOC group was deprotected by stirring with 4N HCl in dioxane solution for 1 h. The solids formed were filtered out washed with ether and dried. To a solution of 300 mg (1.13 mMol) this salt in 10 mL DMF was added 250 mg (1.2 mMol) 4-chlorobenzylbromide and 165 mg (1.2 mMol) of K₂CO₃. The mixture was stirred at RT for 12 h, the product was extracted with ethyl acetate, washed with water and brine. On evaporation and trituration of the residue with EtOAc white solids separated which was collected by filtration. MS (ESI) m/e 353 (M⁺).

B. Following the procedure of paragraph A, but substituting for 4-chlorobenzylbromide, 3-chlorobenzyl bromide, 3-chlorobenzylpiperazinyl)-indole-2-carboxamide was produced.

C. Following the procedure of paragraph A, but substituting, for indole-2-carboxylic acid, indole-5-carboxylic acid, 4-chlorobenzylpiperazinyl)-indole-5-carboxamide was prepared.

EXAMPLE 15

Preparation of 3-Chlorobenzylpiperazinyl-N-benzyl-benzimidazole-5- and 6-carboxamides A. This paragraph describes the procedure for formation of the N-benzyl derivatives of the compounds of the invention; succeeding paragraphs describe alkylation with other moieties.

3-Chlorobenzylpiperazinyl-benzimidazole-5-carboxamide (0.12 g, 0.33 mMol) and the benzyl bromide (0.058 g, 0.33 mMol) in 15 mL DMF were combined with K₂CO₃ (0.09 g, 0.66 mMol). The mixture was stirred at RT overnight, then heated at 45° C. for 3 h. EtOAc was added and washed with water. The organic layer was evaporated and the isomers were separated by silica gel column chromatography using 5% MeOH in EtOAc. of isomer a (70 mg, 48%), MS (ESI) m/e 444 (M⁺) and of isomer b (40 mg, 27%), MS (ESI) m/e 444 (M⁺) were obtained.

B. 3-Chlorobenzylpiperazinyl-N-(2-propyl)-benzimidazole-5- and 6-carboxamides.

3-Chlorobenzylpiperazinyl-benzimidazole-5-carboxamide was alkylated substituting 2-iodopropane for benzyl bromide in paragraph A. The isomers were separated using the same chromatographic conditions. Isomer a, MS (ESI) m/e 396 (M⁺).; isomer b, MS (ESI) m/e 396 (M⁺).

C. 3-Chlorobenzylpiperazinyl-N-methyl-benzimidazole-5- and 6-carboxamide

3-Chlorobenzylpiperazinyl)-benzimidazole-5-carboxamide was alkylated substituting iodomethane for benzyl bromide in the procedure of paragraph A. The isomers were separated using silica gel column chromatography using 50% acetone in acetonitrile as the eluting solvent. Isomer a, MS (ESI) m/e 368 (M⁺), isomer b, MS (ESI) m/e 368 (M⁺).

Similarly, 4-benzylpiperidinyl-(1-methyl)-indole-5-carboxamide (MS (ESI) m/e 332 (M⁺)) was prepared from 4-benzylpiperidinyl-indole-5-carboxamide.

D. 3-Chlorobenzylpiperazinyl-N-ethyl-benzimidazole-5- and 6-carboxamides

3-Chlorobenzylpiperazinyl-benzimidazole-5-carboxamide was alkylated substituting iodoethane for benzyl bromide in paragraph A. Isomer a, MS (ESI) m/e 382 (M⁺); isomer b, MS (ESI) m/e 382 (M⁺).

Similarly, 4-benzylpiperidinyl-(1-ethyl)-indole-5-carboxamide (MS (ESI) m/e 346 (M⁺)) was prepared from 4-benzylpiperidinyl-indole-5-carboxamide.

EXAMPLE 16

Preparation of 4-(4-chlorobenzyl)-piperidinyl-indole-5-carboxamide

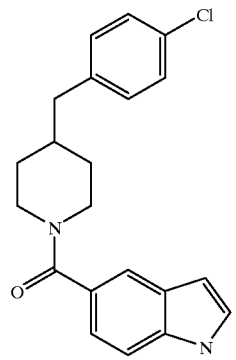

This example illustrates Reaction Scheme 5.

a. Preparation of N-BOC-4-(4-chlorobenzylene)-piperidine

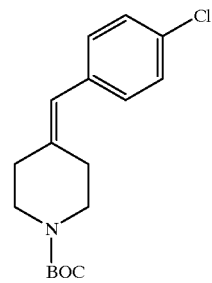

N-BOC-4-piperidone (2.0 g; 10 mmol) was taken with diethyl-4-chlorobenzylphosphonate (2.6 g; 10 mmol ) in dry THF. Sodium hydride (400 mg, 60% dispersion in mineral oil; 10 mmol ) was added and the mixture was refluxed for three h. The THF was removed in vacuo and the residue extracted from water with methylene chloride. The extract was dried over MgSO₄, evaporated and the residue was chromatographed on silica gel to yield 0.615 g of the desired product. ¹HNMR (CDCl₃): δ=7.3 (d, 2H); 7.1 (d, 2H); 6.3 (s, 1H); 3.55–3.50 (m, 2H); 3.45–3.35 (m, 2H); 2.45–2.35 (m, 2H); 2.30–2.25 (m, 2H); 1.25 (s, 9H). EIMS: 307 (M⁺), 251 (M⁺—C3H8).

b. Coupling of 4-Chlorobenzylene piperidine with indole-5-carboxylic acid

The N-BOC-4-(4-chlorobenzylene-piperidine, described above, was deprotected by stirring in 20 mL 1:1 dichloromethane-trifluoroacetic acid for 1 h. It was evaporated and dried in vacuo for 1 h to remove all traces of trifluoroacetic acid. It was redissolved in 15 mL dichloromethane and the TFA salt was neutralized by the addition of a slight excess of triethyl amine. Solution A.

Indole-5-carboxylic acid 0.32 g (2 mmol) was reacted with 0.383 g EDAC in 30 mL dry dichloromethane for 15 minutes. To this solution was added the methylene chloride solution of 4-chlorobenzylene-piperidine (solution A) followed by the addition of 10 mg of DMAP. The mixture was stirred for 20 h. The mixture was washed with water, 2N HCl, 5% sodium carbonate and then water. The organic solution was dried, evaporated and the residue was chromatographed on silica gel eluting with ethylacetate-hexane (1:4). Yield: 260 mg (37%). EIMS: 350 (M$^+$), 315 (M$^+$—Cl) $^1$HNMR (CDCl$_3$): δ=8.4 (s, 1H); 7.7 (s, 1H); 7.3–7.0 (m, 7H); 6.5 (s, 1H); 6.25 (s, 1H); 3.8–3.0 (m, br, 4H); 2.6–2.20 (m, br, 4H).

c. Hydrogenation of 4-(4-chlorobenzylene)-piperidine-indole-5-carboxamide 4-(4-Chlorobenzylene)-piperidine-indole-5-carboxamide (240 mg, 0.68 mmol) was dissolved in 40 mL THF. Pd/C (25 mg) was added and the mixture was hydrogenated (1 atm) for 20 h with rapid stirring. The catalyst was removed by filtration through celite and the organic solution was evaporated and the residue was recrystallized from methylene chloride/hexane. Quantitative yield. EIMS: 352 (M$^+$), 351 (M$^+$—H).

EXAMPLE 17

Using the general procedure set forth in Example 16, the following are prepared:

| Preparation of | Substituting for 4-chlorobenzyl piperidine |
|---|---|
| 4-(3-chlorobenzyl)-piperidinyl-indole-5-carboxamide MS (ESI) m/e 353 (M$^+$) | 3-chlorobenzyl piperidine |
| 4-(2-chlorobenzyl)-piperidinyl-indole-5-carboxamide MS (ESI) m/e 353 (M$^+$) | 2-chlorobenzyl piperidine |

EXAMPLE 18

Synthesis of cis-2-Methyl-4-phenylpiperidin-1-yl-indole-5-carboxamide

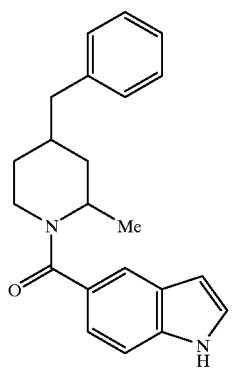

(a) A mixture of 4-benzylpiperidine (3.52 mL, 20.0 mMol) and di-tert-butyl-dicarbonate (5.45 g, 25.0 mMol) in 100 mL of THF was refluxed for 20 h. After cooling to rt the reaction mixture was poured into water and extracted with ethyl acetate (2×100 mL). the combined organic extract was washed with water and brine. The extract was dried over Na$_2$SO$_4$ and evaporated. The residue was chromatographed on a column of silica gel with 10% ethyl acetate-hexane. Evaporation of the desired fractions gave 5.02 g (91%) of the product as an oil. MS (ESI) m/e 275 (M$^+$).

(b) A mixture of 1-BOC-4-benzylpiperidine (0.825 g, 3.0 mMol) and N,N,N',N',-tetramethylethylenediamine (TMEDA) (0.59 mL, 3.9 mMol) in 6 mL of Et$_2$O was cooled to −78° C. under argon. A 1.3M solution of s-BuLi in cyclohexane (3.0 mL, 3.9 mMol) was added dropwise. After the addition was complete, the reaction mixture was stirred at −20° C. for 30 min and cooled back to −78° C. Methyl iodide (0.28 mL, 4.5 mMol) was added and the reaction mixture was stirred at −78° C. for 5 min, the cooling bath removed and stirring was continued an additional 3 min. The reaction mixture was poured into water and extracted with ethyl acetate (2×25 mL). The combined organic extract was washed with water and brine. The extract was dried over Na$_2$SO$_4$ and evaporated to give 0.58 g (67%) of an oil that was one spot by TLC (silica gel, 10% ethyl acetate-hexane). This material was used directly in the next step. MS (ESI) m/e 289 (M$^+$).

(c) To a solution of 1-BOC-2-methyl-4-benzylpiperidine (0.29 g, 1.0 mMol) in 5 mL of dichloromethane was added trifluoroacetic acid (TFA) (0.5 mL). After stirring at rt for 10 h the reaction mixture was evaporated in vacuo and azeotroped twice with dichloromethane and twice with hexane. The residue was dissolved in 5 mL of dichloromethane and diisopropylethylamine (1.6 mL, 10 mMol) was added. In a separate flask a mixture of 5-indolecarboxylic acid (0.19 g, 1.2 mMol) and EDAC (0.23 g, 1.2 mMol) was dissolved in 15 mL of dichloromethane and stirred at rt for 5 min. To this reaction mixture was added the first solution, and the resulting mixture stirred at rt for 20 h. The reaction mixture was poured into water and extracted with ethyl acetate (2×50 mL). The combined organic extract was washed with water and brine. The extract was dried over Na$_2$SO$_4$ and evaporated. The residue was chromatographed on a column of silica gel with 1% MeOH-dichloromethane. Evaporation of the desired fractions gave 0.18 g (54%) of the product as an oil.

When tested as described in Example 19 below, the title compound has an IC$_{50}$=280 nM.

EXAMPLE 19

Assay for p38 Kinase Inhibition

The compounds to be tested were solubilized in DMSO and diluted into water to the desired concentrations. The p38 kinase was diluted to 10 μg/ml into a buffer containing 20 mM MOPS, pH 7.0, 25 mM beta-glycerol phosphate, 2 mg/ml gelatin, 0.5 mM EGTA, and 4 mM DTT.

The reaction was carried out by mixing 20 μl test compound with 10 μl of a substrate cocktail containing 500 μg/ml peptide substrate and 0.2 mM ATP (+200 μCi/ml gamma-32P-ATP) in a 4× assay buffer. The reaction was initiated by the addition of is 10 μl of p38 kinase. Final assay conditions were 25 mM MOPS, pH 7.0, 26.25 mM beta-glycerol phosphate, 80 mM KCl, 22 mM MgCl$_2$, 3 mM MgSO$_4$, 1 mg/ml gelatin, 0.625 mM EGTA, 1 mM DTT, 125 μg/ml peptide substrate, 50 μM ATP, and 2.5 μg/ml enzyme. After a 40 minute incubation at room temperature, the reaction was stopped by the addition of 10 μl per reaction of 0.25 M phosphoric acid.

A portion of the reaction was spotted onto a disk of P81 phosphocellulose paper, the filters were dried for 2 minutes and then washed 4× in 75 mM H$_3$PO$_4$. The filters were rinsed briefly in 95% ethanol, dried, then placed in scintillation vials with liquid scintillation cocktail.

Alternatively, the substrate is previously biotinylated and the resulting reactions are spotted on SAM²™ streptavidin filter squares (Promega). The filters are washed 4× in 2M NaCl, 4× in 2M NaCl with 1% phosphoric acid, 2× in water, and briefly in 95% ethanol. The filter squares are dried and placed in scintillation vials with liquid scintillation cocktail.

Counts incorporated are determined on a scintillation counter. Relative enzyme activity is calculated by subtracting background counts (counts measured in the absence of enzyme) from each result, and comparing the resulting counts to those obtained in the absence of inhibitor. $IC_{50}$ values were determined with curve-fitting plots available with common software packages. Approximate $IC_{50}$ values were calculated using formula $$IC_{50}(app)=A \times i/(1-A)$$

where A=fractional activity and i=total inhibitor concentration.

EXAMPLE 20

Comparison of Invention Compounds to Compounds in the Prior Art

As set forth above, WO98/06715 describes 3-carboxy indole piperazine and 4-carboxy indole piperazine-containing compounds for use as antiinflammatory agents and inhibitors of p38 kinase-mediated diseases. When tested in the above assay with regard to activity for p38α, it was shown that the compounds of the invention, containing piperidinyl residues, were consistently more potent inhibitors of p38α than the corresponding piperazines. These results are shown in Table 1 as $IC_{50}$ in μM for inhibition of p38α.

All of the compounds in the table are 4-(4-benzyl piperidinyl)- or 4-(4-benzyl piperazinyl)-indole carboxamides. The point of attachment of the carboxamide residue in the indole nucleus is shown in column 1 of the table. Thus, for example, the first pair of compounds in the table, represented by ring position 2, are 4-(4-benzyl piperidinyl)-indole-2-carboxamide and 4-(4-benzyl piperazinyl)-indole-2-carboxamide.

TABLE 1

| Ring position | Piperidinyl $IC_{50}$ μM | Piperazinyl $IC_{50}$ μM | Fold increase Piperidinyl/Piperazinyl |
|---|---|---|---|
| 2 | 2.66 | >30 | >11.3 |
| 3 | 0.163 | 4.74 | 29.1 |
| 4 | 0.159 | 1.54 | 9.7 |
| 5 | 0.150 | 1.71 | 11.4 |
| 6 | 0.462 | 5.52 | 11.9 |
| 7 | 7.04 | >30 | >4.3 |

The same compounds were tested for their specificity for p38α as compared to p38β. The results are shown in Table 2.

TABLE 2

| | Piperidinyl | | | Piperazinyl | | |
|---|---|---|---|---|---|---|
| Ring position | P38-β $IC_{50}$ μM | p38α $IC_{50}$ μM | $IC_{50}$ ratio β/α | P38-β $IC_{50}$ μM | p38-α $IC_{50}$ μM | $IC_{50}$ ratio β/α |
| 2 | | 2.66 | | | >30 | |
| 3 | 1.77 | 0.163 | 10.9 | 34.0 | 4.74 | 7.17 |

TABLE 2-continued

| | Piperidinyl | | | Piperazinyl | | |
|---|---|---|---|---|---|---|
| Ring position | P38-β $IC_{50}$ μM | p38α $IC_{50}$ μM | $IC_{50}$ ratio β/α | P38-β $IC_{50}$ μM | p38-α $IC_{50}$ μM | $IC_{50}$ ratio β/α |
| 4 | 2.43 | 0.159 | 15.3 | 24.0 | 1.54 | 15.6 |
| 5 | 3.02 | 0.150 | 20.1 | 25.8 | 1.71 | 15.1 |
| 6 | 3.83 | 0.462 | 8.27 | 39.1 | 5.52 | 7.08 |
| 7 | | 7.04 | | | >30 | |

The compounds of the invention as well as those containing piperazine, generally, are specific for p38α as compared to p38β. In the case of coupling both to ring positions 2 and 7 the $IC_{50}$s for the β form were not measured for both the piperazines and the piperidines. It is seen that the specificity for α as opposed to β is generally of the order of ten-fold.

The specificity of the compounds of the invention was also tested with respect to other kinases, including p38-γ, ERK-2, PKA, PKC, cdc-2, EGF-R, and DNA-PK as shown in Table 3. The compounds indicated as 5, 3, 4 and 6 are the same as those set forth in Tables 1 and 2—i.e., they are the 4-(4-benzyl piperidinyl)-indole carboxamides with the number indicating the ring position of the carboxamide.

TABLE 3

| KINASE | $IC_{50}$ μM 5 | $IC_{50}$ μM 3 | $IC_{50}$ μM 4 | $IC_{50}$ μM 6 |
|---|---|---|---|---|
| p38-α | 0.150 | 0.163 | 0.159 | 0.462 |
| p38-γ | 228 | 177 | >300 | >300 |
| ERK-2 | >300 | >300 | >300 | >300 |
| PKA | 430 | 470 | 430 | >500 |
| PKC | >500 | >500 | >500 | >500 |
| cdc2 | >500 | >500 | >500 | >500 |
| EGF-R | >500 | >500 | >500 | >500 |
| DNA-PK | >500 | >500 | >500 | 450 |

The results are given in terms of approximate $IC_{50}$ (μM) values when the compounds were tested at 50 μM except for p38α which is based on $IC_{50}$ curves.

As shown, all of the compounds tested are highly specific for p38α as compared to these additional kinases.

What is claimed is:

1. A compound of the formula:

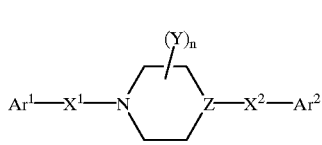

(1)

and the pharmaceutically acceptable salts thereof
wherein $Ar^1$ is indole, benzimidazole, or benzotriazole, optionally substituted with lower alkyl (1–4C), halo, or lower alkoxy (1–4C);
when $Ar^1$ is benzimidazole, $Ar^1$ is coupled to $X^1$ through the 3, 4, 5, or 6 position;
when $Ar^1$ is indole, $Ar^1$ is coupled to $X^1$ through the 5 or 6 position;
$X^1$ is CO, SO, $SO_2$ or CHOH;
Y is optionally substituted alkyl, optionally substituted aryl, or optionally substituted arylalkyl;
n is 0 or 1;

Z is CH;
X² is CH, X¹; and
Ar² consists of one or two phenyl moieties directly coupled to X² and optionally substituted by halo, nitro, alkyl (1–6C), CN or CF₃, or by RCO, COOR, CONR₂, NR₂, OR or SR, wherein R is H or alkyl (1–6C) or by phenyl, itself optionally substituted by the foregoing substituents.

2. The compound of claim 1 wherein n is 0.

3. The compound of claim 1 wherein X¹ is CO.

4. The compound of claim 1 wherein Ar¹ is indole or benzimidazole.

5. The compound of claim 1 wherein benzotriazole is coupled to X¹ through the 3, 4, 5 or 6 position.

6. The compound of claim 1 wherein X² is CH and Ar² consists of two optionally substituted phenyl moieties.

7. The compound of claim 1 wherein X² is CH₂ or CO and Ar² consists of one optionally substituted phenyl moiety.

8. The compound of claim 1 wherein Ar² is phenyl optionally substituted with halo.

9. The compound of claim 1 wherein Ar¹ is coupled to X¹ through its 5-position.

10. The compound of claim 9 wherein X¹ is CO.

11. The compound of claim 9 wherein n is 0.

12. The compound of claim 9 wherein Ar¹ is optionally substituted indole or benzimidazole.

13. The compound of claim 9 wherein Ar¹ is optionally substituted indole.

14. The compound of claim 9 wherein X² is CH₂ or CO and Ar² consists of one optionally substituted phenyl moiety.

15. The compound of claim 9 wherein Ar² is phenyl optionally substituted with halo.

16. The compound of claim 1 wherein Ar¹ is optionally substituted indole.

17. The compound of claim 16 wherein Ar¹ is unsubstituted indole.

18. The compound of claim 16 wherein X¹ is CO.

19. The compound of claim 16 wherein n is 0.

20. The compound of claim 16 wherein X² is CH and Ar² consists of two optionally substituted phenyl moieties.

21. The compound of claim 16 wherein X² is CH₂ and Ar² consists of one optionally substituted phenyl moiety.

22. The compound of claim 16 wherein Ar¹ is phenyl optionally substituted with halo.

23. The compound of claim 1 wherein Ar¹ is optionally substituted benzimidazole.

24. The compound of claim 23 wherein X¹ is CO.

25. The compound of claim 23 wherein n is 0.

26. The compound of claim 23 wherein X² is CH and Ar² consists of two optionally substituted phenyl moieties.

27. The compound of claim 23 wherein X² is CH₂ and Ar² consists of one optionally substituted phenyl moiety.

28. The compound of claim 23 wherein Ar² is phenyl optionally substituted with halo.

29. The compound of claim 1 which is 4-benzylpiperidinyl-indole-5-carboxamide or is 4-benzylpiperidinyl-benzimidazole-5-carboxamide.

30. A method to treat a condition characterized by a proinflammation response associated with activation of a p38 kinase receptor which method comprises administering to a subject in need of such treatment the compound defined in claim 1.

31. The method of claim 30 wherein said condition characterized by inflammation is acute respiratory distress syndrome, asthma, chronic obstructive pulmonary disease, uveitis, IBD, acute renal failure, head trauma, or ischemic/reperfusion injury.

32. The method of claim 30 wherein said condition is acute respiratory distress syndrome, asthma, chronic obstructive pulmonary disease, uveitis, IBD, acute renal failure, head trauma, or ischemic/reperfusion injury.

33. A method to treat a heart condition associated with cardiac failure which method comprises administering to a subject in need of such treatment a compound of the formula (1)

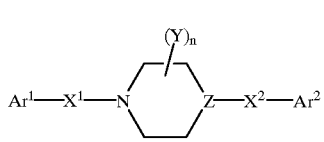

or a pharmaceutically acceptable salt thereof
wherein Ar¹ is indole, benzimidazole, or benzotriazole, optionally substituted with lower alkyl (1–4C), halo, or lower alkoxy (1–4C);
X¹ is CO, SO, SO₂, CH₂ or CHOH;
Y is optionally substituted alkyl, optionally substituted aryl, or optionally substituted arylalkyl;
n is 0 or 1;
Z is CH;
X² is CH, CH₂ or an isostere thereof; and
Ar² consists of one or two phenyl moieties directly coupled to X² and optionally substituted by halo, nitro, alkyl (1–6C), CN or CF₃, or by RCO, COOR, CONR₂, NR₂, OR or SR, wherein R is H or alkyl (1–6C) or by phenyl, itself optionally substituted by the foregoing substituents.

34. The method of claim 33 wherein said chronic heart condition is congestive heart failure, cardiomyopathy or myocarditis.

35. A method to treat excessive activity of p38-α kinase in coronary artery disease, congestive heart failure, cardiomyopathy, myocarditis, coronary angioplasty, heart failure, cardiopulmonary bypass, or coronary artery bypass graft comprises administering to a subject in need of such treatment a p38-α kinase inhibitory effective amount of a compound of the formula (1)

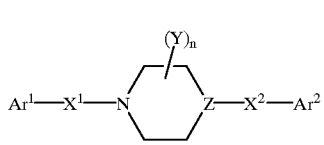

or a pharmaceutically acceptable salt thereof
wherein Ar¹ is indole, benzimidazole, or benzotriazole, optionally substituted with lower alkyl (1–4C), halo, or lower alkoxy (1–4C);
X¹ is CO, SO, SO₂, CH₂ or CHOH;
Y is optionally substituted alkyl, optionally substituted aryl, or optionally substituted arylalkyl;
n is 0 or 1;
Z is CH;
X² is CH, CH₂ or X²; and
Ar² consists of one or two phenyl moieties directly coupled to X² and optionally substituted by halo, nitro, alkyl (1–6C), CN or CF₃, or by RCO, COOR, CONR₂, NR₂, OR or SR, wherein R is H or alkyl (1–6C) or by phenyl, itself optionally substituted by the foregoing substituents.

36. The method defined in claim 35 wherein said excessive activity is characterized by a proinflammation response.

37. The method defined in claim 35 wherein said excessive activity is in a heart condition associated with cardiac failure.

38. The method of claim 37 wherein said chronic heart condition is congestive heart failure, cardiomyopathy or myocarditis.

39. A method to prepare the compound defined in claim 1 which method comprises (a) reacting a compound of the formula $$Ar^1-COOH \qquad (2)$$

with a compound of the formula

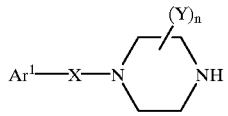

(3)

under conditions wherein the carboxamide is formed; or (b) reacting an optionally substituted indole, benzimidazole or benzotriazole with a compound of the formula

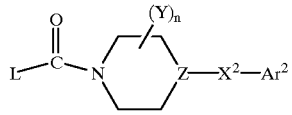

(4)

wherein L is leaving group; or (c) reacting a compound of the formula (5)

with a compound of the formula $$Ar^2-X^2-M \qquad (6)$$

wherein M is a halide, under conditions of mild base.

* * * * *

UNITED STATES PATENT AND TRADEMARK OFFICE

CERTIFICATE OF CORRECTION

PATENT NO. : 6,130,235

DATED : Oct. 10, 2000

INVENTOR(S) : Babu J. Mavunkel et al.

It is certified that error appears in the above-identified patent and that said Letters Patent is hereby corrected as shown below:

Claim 1, column 29, line 2, after "CH," insert --$CH_2$ or--.

Claim 22, line 43, change "$Ar^1$" to --$Ar^2$--.

Claim 32, line 1, after "condition" insert --characterized by inflammation--.

Claim 33, line 26, after "or" delete "an isostere thereof" and add --$X^1$--.

Signed and Sealed this

Twenty-second Day of May, 2001

*Attest:*

NICHOLAS P. GODICI

*Attesting Officer*   *Acting Director of the United States Patent and Trademark Office*